United States Patent [19]

King

[11] Patent Number: 4,959,367
[45] Date of Patent: Sep. 25, 1990

[54] 4-OXO-1,2,3-BENZOTRIAZINES

[75] Inventor: Francis D. King, Bishop's Stortford, England

[73] Assignee: Beecham Group P.L.C., Middlesex, England

[21] Appl. No.: 266,122

[22] Filed: Nov. 2, 1988

[30] Foreign Application Priority Data

Nov. 4, 1987 [GB] United Kingdom ............... 8725840
Feb. 11, 1988 [GB] United Kingdom ............... 8803110

[51] Int. Cl.[5] .................. C07D 401/04; C07D 401/14; C07D 403/04; A61K 31/53
[52] U.S. Cl. .................. 514/243; 514/183; 514/214; 514/216; 544/183; 544/184; 540/478; 540/585
[58] Field of Search ............... 544/249, 250, 251, 287, 544/288, 183, 184; 540/478, 582; 514/259, 267, 214, 183, 216, 243

[56] References Cited

FOREIGN PATENT DOCUMENTS 94742 11/1983 European Pat. Off. .
84/01151 3/1984 World Int. Prop. O. .

Primary Examiner—John M. Ford
Attorney, Agent, or Firm—Hopgood, Calimafde, Kalil, Blaustein & Judlowe

[57] ABSTRACT

Compounds of formula (I) and pharmaceutically acceptable salts thereof:

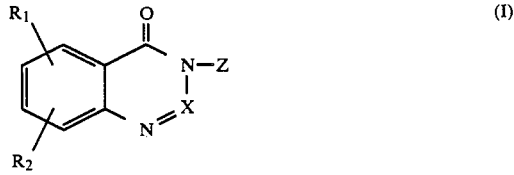

wherein
X is N or CH;
$R_1$ and $R_2$ are the same or different and are hydrogen, halogen, $CF_3$, $C_{1-6}$ alkyl, $C_{1-7}$ acyl, $C_{1-7}$ acylamino, or amino, aminocarbonyl or aminosulphonyl, optionally substituted by one or two $C_{1-6}$ alkyl or $C_{3-8}$ cycloalkyl groups, or by $C_{4-5}$ polymethylene or by phenyl, $C_{1-6}$ alkylsulphonyl, $C_{1-6}$ alkylsuphinyl, $C_{1-6}$ alkoxy, $C_{1-6}$ alkylthio, hydroxy or nitro; or $R_1$ and $R_2$ taken together are methylenedioxy or ethylenedioxy;
Z is a group of formula (a), (b) or (c)

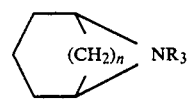

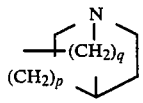

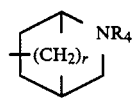

wherein
n is 2 or 3; p is 1 or 2; q is 1 to 3; r is 1 to 3; and
$R_3$ or $R_4$ is $C_{1-4}$ alkyl;
having 5-$HT_3$ receptor antagonist activity, a process for their preparation and their use as pharmaceuticals.

10 Claims, No Drawings

4-OXO-1,2,3-BENZOTRIAZINES

This invention relates to novel compounds having useful pharmacological properties, to pharmaceutical compositions containing them, to a process and intermediates for their preparation, and to their use as pharmaceuticals.

EP-A-220011 (Beecham Group p.l.c.) describes a class of benzamides having an azabicyclic side chain, and possessing 5-HT₃ receptor antagonist activity, and gastric motility enhancing activity.

A class of novel, structurally distinct compounds has now been discovered. These compounds have 5-HT₃ receptor antagonist activity and gastric motility enhancing activity.

Accordingly, the present invention provides a compound of formula (I), or a pharmaceutically acceptable salt thereof:

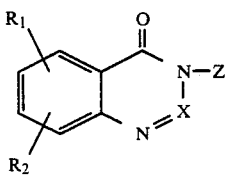

wherein
X is N or CH;
$R_1$ and $R_2$ are the same or different and are hydrogen, halogen, $CF_3$, $C_{1-6}$ alkyl, $C_{1-7}$ acyl, $C_{1-7}$ acylamino, or amino, aminocarbonyl or aminosulphonyl, optionally substituted by one or two $C_{1-6}$ alkyl or $C_{3-8}$ cycloalkyl groups, or by $C_{4-5}$ polymethylene or by phenyl, $C_{1-6}$ alkylsulphonyl, $C_{1-6}$ alkylsuphinyl, $C_{1-6}$ alkoxy, $C_{1-6}$ alkylthio, hydroxy or nitro; or $R_1$ and $R_2$ taken together are methylenedioxy or ethylenedioxy;
Z is a group of formula (a), (b) or (c)

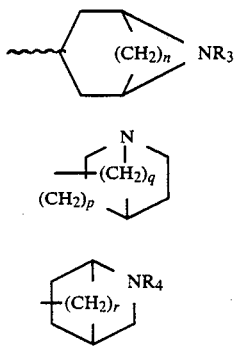

wherein
n is 2 or 3; p is 1 or 2; q is 1 to 3; r is 1 to 3; and $R_3$ or $R_4$ is $C_{1-4}$ alkyl.
Preferably X is N.

Suitable examples of the groups $R_1$ and $R_2$ include the following groups; hydrogen, chlorine, bromine, methyl, ethyl, amino, methylamino, dimethylamino, $C_{1-4}$ alkanoylamino such as formylamino, acetylamino, propionylamino, n- and iso-butyrylamino, aminosulphonyl, and amino and aminosulphonyl substituted by one or two methyl, ethyl, n- or iso-propyl, n-, sec-, iso- or tert-butyl or phenyl groups, nitro, methoxy, ethoxy, n- and iso-propoxy, methylthio, ethylthio, n- and iso-propylthio, hydroxy, methylsulphonyl and ethylsulphonyl.

Particularly suitable $R_1$ and $R_2$ groups include hydrogen, halogen, methoxy, optionally substituted amino and aminosulphonyl as defined and $C_{1-6}$ alkylsulphonyl.

It is generally preferred that $R_1$ is in the 6-position and $R_2$ is in the 7-position.

Preferred $R_2$ groups include hydrogen, 7-halo, such as 7-bromo and 7-chloro, and 7-amino. $R_1$ groups of interest include optionally substituted 6-aminosulphonyl as defined and 6-$C_{1-6}$ alkylsulphonyl or -sulphinyl, such as 6-aminosulphonyl and 6-methylsulphonyl, hydrogen, and 6-halo as for $R_2$ 7-halo.

When $R_1$ and $R_2$ taken together are methylenedioxy or ethylenedioxy, $R_1$ and $R_2$ are preferably ethylenedioxy.

Often the 3-nitrogen and the side chain nitrogen atom are separated by 2, 3 or 4 carbon atoms, preferably 2 or 3. Examples of $R_3/R_4$ are methyl, ethyl, n- and iso-propyl, n-, iso-, sec- and tert-butyl, preferably methyl.

Preferably n is 2 and p, q and r are 1 or 2.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, lactic, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_a$-T wherein $R_a$ is $C_{1-6}$ alkyl, phenyl-$C_{1-6}$ alkyl or $C_{5-7}$ cycloalkyl, and T is a radical corresponding to an anion of an acid. Suitable examples of $R_a$ include methyl, ethyl and n- and iso-propyl; and benzyl and phenethyl. Suitable examples of T include halide such as chloride, bromide and iodide.

Examples of pharmaceutically acceptable salts of compounds of formula (I) also include internal salts such as pharmaceutically acceptable N-oxides. The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that the benzodi/tri-azinone nucleus in compounds of formula (I) may adopt an endo or exo configuration with respect to Z. The endo configuration is preferred.

A group of compounds within formula (I) is of formula (II):

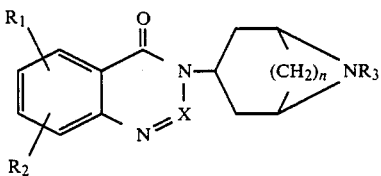

wherein the variables are as defined in formula (I).

Examples of the variables and preferred variables are as so described for corresponding variables in relation to formula (I).

A further group of compounds within formula (I) is of formula (III):

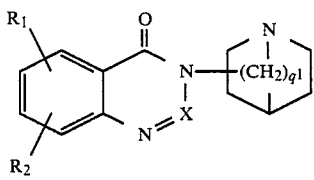

wherein $q^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

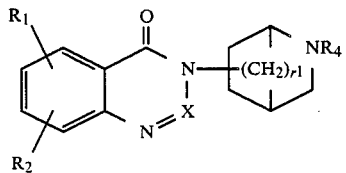

wherein $r^1$ is 1 or 2 and the remaining variables are as defined in formulae (I) and (II).

Examples of the variables and preferred variables are so described as the corresponding variables in formula (I).

The invention also provides a process for the preparation of a compound of formula (I), or a pharmaceutically acceptable salt thereof, which process comprises cyclising a compound of formula (V):

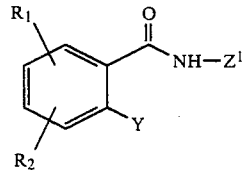

wherein (when X is N), Y is a group $-N_2^+L^-$ wherein $L^-$ is an anion of an acid; or (when X is CH), Y is a group $-NHCHQ_1Q_2$ where $Q_1$ and $Q_2$ are both leaving groups, or $Q_1$ and $Q_2$ together form an oxo group; $Z^1$ is Z as defined or Z wherein $R_3/R_4$ is replaced by a hydrogenolysable protecting group; and the remaining variables are as hereinbefore defined; and thereafter converting $Z^1$, when other than Z, to Z; optionally converting $R_3$ and/or $R_4$ to other $R_3$ and/or $R_4$; and optionally forming a pharmaceutically acceptable salt of the resultant compound of formula (I).

The counter-ion $L^-$ is generally a strong inorganic acid anion such as chloride, bromide, hydrogen sulphate, or a complex polyhalo anion, such as tetrafluoroborate or hexafluorophosphate.

Suitable values for $Q_1$ and $Q_2$ include $C_{1-4}$ alkoxy, such as ethoxy or $Q_1$ and $Q_2$ together form an oxo group.

When Y is $-N_2^+L^-$ as defined, the compound of the formula (XXII) is often present in aqueous acidic solution having been prepared in situ by conventional diazotisation. Basification for example with an alkali metal hydroxide such as sodium hydroxide or an alkali metal weak acid salt such as sodium acetate generally effects cyclisation.

When $Q_1$ and $Q_2$ are such a group readily displaceable by a nucleophile, for example $C_{1-4}$ alkoxy, or together are oxo, cyclisation is generally effected in an inert solvent by heating under acid or base catalysis to a non-extreme elevated temperature, for example under solvent reflux. The compound of formula (V) is often generated in situ especially when $Q_1$ and $Q_2$ together are oxo, and in these cases the solvent will be that used in the preparation, or an excess of one of the preparative reagents.

The (in situ) preparation of compounds of the formula (V) is described hereinafter.

It will be apparent that compounds of the formula (I) containing an $R_1$ or $R_2$ group which is convertible to another $R_1$ or $R_2$ group are useful novel intermediates.

The skilled person will appreciate that the choice or necessity of conversion of groups $R_1$ and/or $R_2$ to other groups $R_1$ and/or $R_2$ will be dictated by the nature and position of substituents $R_1$ and/or $R_2$.

It will be apparent that compounds of the formula (I) containing an $R_1$ or $R_2$ group which is convertible to another $R_1$ or $R_2$ group are useful intermediates, and as such form an important aspect of the invention. By way of example of such conversions, the compounds of the formula (I) wherein $R_1$ or $R_2$ is a nitro group may be prepared via the nitration of the corresponding intermediate product wherein $R_1$ or $R_2$ is a hydrogen atom.

Also the reduction of the intermediates wherein $R_1$ or $R_2$ is a nitro group to $R_1/R_2$ amino may be effected with reagents known to be suitable for reducing nitroarenes to aminoarenes.

Those compounds of the invention wherein $R_1$ or $R_2$ is a $C_{1-7}$ acylamino group may be prepared from the corresponding intermediate wherein $R_1$ or $R_2$ is an amino group by reaction with a conventional acylating derivative. For an $R_1/R_2$ fromamido group acylation may be effected with the free acid.

This invention thus also provides an optional process (I) wherein $R_1$ or $R_2$ is an amino group which process comprises the deacylation of a corresponding intermediate wherein $R_1$ or $R_2$ is a $C_{1-7}$ acylamino group.

Generally the hydrolysis reaction may be effected by treatment with a base such as an alkali metal hydroxide.

Also a compound of the formula (I) wherein $R_1$ or $R_2$ is halogen may be prepared by a conventional halogenation of the corresponding intermediate wherein the said $R_1$ or $R_2$ is hydrogen.

Similarly the compounds wherein $R_1$ or $R_2$ is $C_{1-6}$ alkylthio or $C_{1-6}$ alkylsulphinyl may be oxidised to the corresponding compounds wherein $R_1$ or $R_2$ is $C_{1-6}$ alkylsulphinyl or $C_{1-6}$ alkylsulphonyl respectively. These oxidations may conveniently be carried out conventionally at below ambient temperatures using an organic peracid in a non-aqueous inert reaction medium, preferably a chlorinated hydrocarbon solvent, for example using 3-chloroperbenzoic acid, or using a water soluble inorganic strong oxidant, such as an alkali metal permanganate or hydrogen peroxide in aqueous solution.

It will be appreciated that, depending on the other specific substituents in the compound of the formula (I), such an oxidation on a compound of the formula (I) may also form the N-oxide of the bicyclic moiety therein.

Given the specific substitution desired and it having been decided whether the compound or its N-oxide is required, the skilled man will readily ascertain whether such $R_1/R_2$ interconversion is desirable. In general it is preferred to effect the oxidation in the intermediate of formula (VIII) as hereinafter defined.

$Z^1$ when other than Z may have a hydrogenolysable protecting group which is benzyl optionally substituted by one or two groups independently selected from halogen, $C_{1-4}$ alkoxy, $C_{1-4}$ alkyl or nitro. Such benzyl groups may, for example, be removed, when $R_1/R_2$ is not halogen, by conventional transition metal catalysed hydrogenolysis to give compounds of the formula (VI):

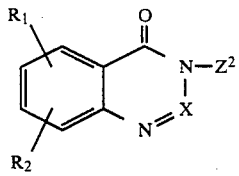
(VI)

wherein $Z^2$ is of formula (d) or (e)

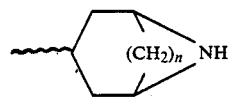
(d)

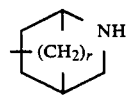
(e)

wherein the variables are as defined in formula (I).

This invention also provides a further process for the preparation of a compound of the formula (I) which comprises N-alkylating a compound of formula (VI), and optionally forming a pharmaceutically acceptable salt, of the resulting compound of the formula (I).

This may be achieved by reaction of the compound of formula (VI) with a compound $R_3Q_3$ or $R_4Q_3$ wherein $R_3$ and $R_4$ are as hereinbefore defined and $Q_3$ is a leaving group.

Suitable values for $Q_3$ include groups displaced by nucleophiles such as Cl, Br, I, $OSO_2CH_3$, $OSO_2C_6H_4pCH_3$ or $OSO_3CH_3$.

Favoured values for $Q_3$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slightly above.

Alternatively, 'N-alkylation' may be effected under conventional reductive alkylation conditions when the group $R_3$ or $R_4$ in the compound of formula (I) contains a methylene group adjacent to the N-atom in the bicycle.

Interconverting $R_3$ or $R_4$ in the compound of the formula (VI) before cyclisation of the compound of formula (V) or on the compound of formula (IX) before coupling with the compound of formula (VIII) as described hereinafter, is also possible. Such interconversions are effected conveniently under the above conditions. It is desirable to protect any amine function with a group readily removable by acidolysis such as a $C_{2-7}$ alkanoyl group, before $R_3/R_4$ interconversion.

The preparation of intermediates for the above preparative processes will now be described.

Where Y is $N_2+L^-$ as defined, the compound of the formula (V) is usually generated in situ in solution by the diazotisation of the corresponding amine of formula (VII):

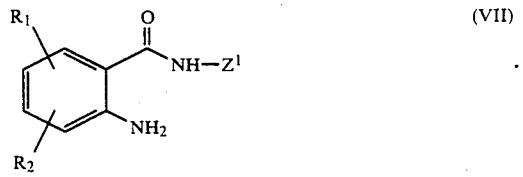
(VII)

Diazotisation may be carried out conventionally, for example, by the interaction of an alkali metal nitrite, a strong inorganic acid and the compound of the formula (VII) in aqueous solution at 10° to −10° C.

When Y is $NHCHQ_1Q_2$ where $Q_1$ and $Q_2$ are each $C_{1-4}$ alkoxy, for example ethoxy, the intermediate of formula (V) may be prepared in situ by known methods, such as by reacting the compound of the formula (VII) with a tri-($C_{1-4}$ alkyl) orthoformate.

When $Q_1$ and $Q_2$ together are an oxo group, the reaction is preferably carried out by heating a mixture of the compound of formula (VII) with formic acid at e.g. reflux, using excess of acid as solvent.

Compounds of the formula (VII), in this case, are prepared in situ by reacting compounds of the formula (VIII):

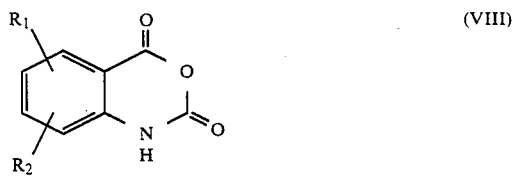
(VIII)

with a compound of the formula (IX):

$H_2N-Z^1$ (IX)

heating to a non-extreme temperature in an inert solvent.

An alternative method for the preparation of a compound of formula (VII) is by the reduction of a compound of the formula (X):

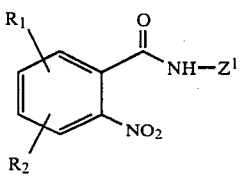

The reduction may be effected using conventional methods for reducing nitro groups on aromatic nuclei, for example using Raney nickel, or by the ammonolysis of a corresponding compound of the formula (X) wherein the 2-nitro group is replaced by halo, such as fluoro or chloro, preferably fluoro. The ammonolysis may be effected conventionally.

The compounds of the formulae (VII) and (X) may be prepared by the reaction of a compound of the formula (XI):

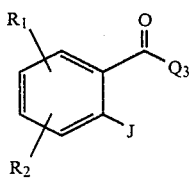

wherein J is $NH_2$ or $NO_2$; $Q_3$ is a leaving group and the remaining variables are as defined in formula (I); with a compound of (IX) as hereinbefore defined.

Examples of leaving groups $Q_3$, displaceable by a nucleophile, include halogen such as chloro and bromo; $C_{1-4}$ alkoxy, such as $CH_3O$ and $C_2H_5O-$; PhO-; activated hydrocarbyloxy, such as $Cl_5C_6O-$ or $Cl_3CO-$; succinimidyloxy; and imidazolyl. Preferably $Q_1$ is halogen, most preferably chloro.

If a group $Q_3$ is a halide or imidazolyl, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°-100° C., in particular 10°-80° C. are suitable.

If a group $Q_3$ is $C_{1-4}$ alkoxy, phenoxy, activated hydrocarbyloxy or succinimidyloxy then the reaction is preferably carried out in an inert solvent, such as toluene or dimethylformamide. In this instance, it is preferred that the group $Q_1$ is $Cl_3CO-$ or succinimidyloxy and that the reaction is carried out in toluene at reflux temperature.

The compounds of formula (VIII) and (IX) are known or are preparable analogously to, or routinely from, known compounds.

Compounds of the formulae (V), (VII) and (X) are novel and form an aspect of the invention.

It will be realised that in the compound of the formula (I) the benzodi/tri-azinone nucleus may adopt an endo or exo (axial or equatorial) orientation with respect to the ring of the bicyclic moiety to which it is attached. A mixture of endo and exo isomers of the compound of the formula (I) may be synthesised non-stereospecifically and the desired isomer separated conventionally therefrom e.g. by chromatography; or alternatively the endo and exo isomer may if desired be synthesised from the corresponding endo or exo form of the compound of the formula (IX).

Pharmaceutically acceptable salts of the compounds of this invention may be formed conventionally. The acid addition salts may be formed for example by reaction of the base compound of formula (I) with a pharmaceutically acceptable organic or inorganic acid.

The compounds of the present invention are 5-$HT_3$ receptor antagonists and it is thus believed may generally be used in the treatment or prophylaxis of emesis, migraine, cluster headaches, trigeminal neuralgia, visceral pain and anxiety. Compounds which are 5-$HT_3$ receptor antagonists may also be of potential use in the treatment of other CNS disorders such as psychosis; drug withdrawal syndrome, arrhythmia, obesity and gastrointestinal disorders such as irritable bowel syndrome.

Anti-emetic activity, in particular, includes that of preventing cytotoxic agent or radiation induced nausea and vomiting. Examples of cytotoxic agents include cisplatin, doxorubicin and cyclophosphamide.

The compounds of the present invention also have gastric motility enhancing activity, useful in the treatment of disorders such as retarded gastric emptying, dyspepsia, flatulence, oesophagal reflux and peptic ulcer.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol;

preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of emesis, migraine, cluster headache, trigeminal neuralgia, visceral pain and/or anxiety in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70kg adult will normally contain 0.05 to 1000 mg for example 0.1 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of emesis, migraine, cluster headache, trigeminal neuralgia, visceral pain and/or anxiety.

The following Examples illustrate the preparation of compounds of formula (I); the following descriptions illustrate the preparation of intermediates.

DESCRIPTION 1

(endo)-2-Amino-5-chloro-N-(8-methyl-8-azabicyclo[3.2.1]oct-3-yl)-1-benzamide (D1)

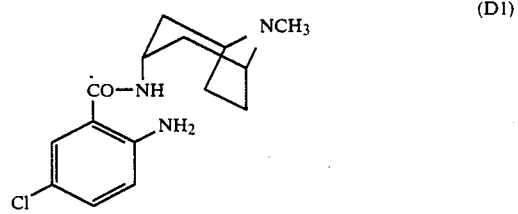

A solution of 5-chloroisatoic anhydride (2.82 g) and (endo)-8-methyl-8-azabicyclo[3.2.1]octane-3-amine (2 g) in dry dimethylformamide (50 ml) was heated at 50° C. for 1 h. The reaction mixture was cooled and the solvent evaporated under reduced pressure. The residue was partitioned between chloroform and water. The organic phase was separated, dried ($Na_2SO_4$) and the solvent was then evaporated under reduced pressure. The product was crystallised from ethyl acetate to give the title compound (D1) (1.2 g, 30%) m.p. 151°-2° C. $^1$H-NMR ($CDCl_3$) 270 MHz.

| δ | |
|---|---|
| | 7.20–7.10 (m, 2H) |
| | 6.60 (d, 1H) |
| | 6.40–6.20 (m, 1H) |
| | 5.45 (bs, 2H) |
| | 4.20 (q, 1H) |
| | 3.25–3.10 (m, 2H) |
| | 2.30 (s, 3H) |
| | 2.35–2.05 (m, 4H) |
| | 1.95–1.60 (m, 4H) |

DESCRIPTION 2

5-Chloro-4-nitroanthranilic acid (D2)

(Span. 371,070; C.A. P14141c[1972])

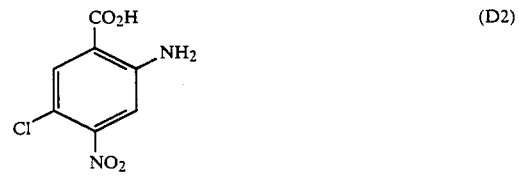

2-Acetamido-5-chloro-4-nitrobenzoic acid (16 g, 0.062mol) was hydrolysed in 10% sodium hydroxide solution (60 ml) and water (40 ml) at 90° C. for two hours. The dark brown solution was cooled and acidified with 5N hydrochloric acid. The resulting brown precipitate was collected and dried in vacuo over $P_2O_5$ to give the title compound (12.3 g, 92%).

DESCRIPTION 3

(endo)-N-(8-Methyl-8-azabicyclo[3.2.1.oct-3-yl)-2-amino-5-chloro-4-nitrobenzamide (D3)

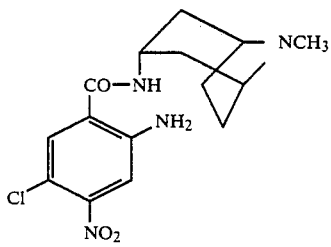

(D3)

5-Chloro-4-nitroanthranilic acid (5.0 g, 0.023 mol) was dissolved in dry THF (150 ml). 12.5% Phosgene in toluene solution (50 ml) was added dropwise over a 30 minute period. Once addition was complete the mixture was heated to about 50° C. The reaction was kept at this temperature for four hours and then cooled. The solution was evaporated to dryness and azeotroped twice with toluene (100 ml). The resulting residue was dissolved in dry DMF (100 ml) and the tropane amine (3.3 g, 0.023 mol) was added. The mixture was heated to 100° C. for two hours and then stirred at room temperature for 48 hours. The DMF was removed in vacuo and 10% potassium carbonate solution was added. The product was extracted into chloroform (2×200 ml) and dried over sodium sulphate. Evaporation to dryness gave the crude product which was purified by column chromatography on alumina, eluting with chloroform. This gave the title compound (1.2 g, 15%).

DESCRIPTION 4

(endo)-N-(9-methyl-9-azabicyclo[3.3.1]non-3-yl)-2-amino-5-chloro-4-nitrobenzamide (D4)

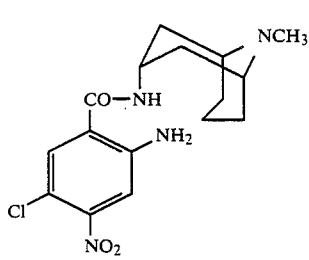

(D4)

5-Chloro-4-nitroanthranilic acid (2.0 g, 0.0092 mol) was refluxed in toluene (65 ml) with thionyl chloride (20 ml) for four hours. The solution was cooled, evaporated to dryness and azeotroped once with toluene (50 ml). The residue was dissolved in methylene chloride (100 ml) and the granatane amine (1.46 g, 0.0095 mol) was added. The mixture was stirred at room temperature for 20 hours, washed with sodium bicarbonate solution and dried over sodium sulphate. The residue after evaporation was purified by column chromatography on alumina (100 g), eluting with chloroform, to give the title compound (1.37 g, 40%).

EXAMPLE 1

(endo)-3-(8-Methyl-8-azabicyclo[3.2.1]oct-3-yl)-6-chloro-3,4-dihydro-4-oxo-1,2,3-benzotriazine (E1)

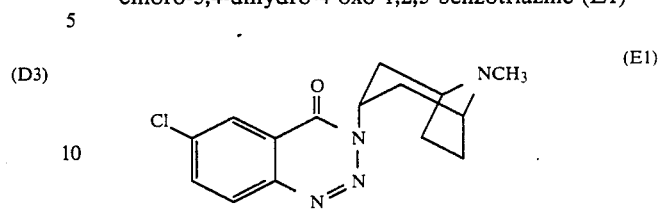

(E1)

A solution of sodium nitrite (0.3 g) in water (3 ml) was added dropwise to a solution of (endo)-2-amino-5-chloro-N-(8-methyl-8-azabicyclo[3.2.1]oct-3-yl)-1-benzamide (D1) (1.12 g) in conc. hydrochloric acid (3 ml) at 0° C. The reaction mixture was stirred at 0° C. for 1½ h and then basified with potassium carbonate solution. The product was extracted into dichlomethane (2×100 ml). The organic phase was dried Na$_2$SO$_4$) and the solvent evaporated under reduced pressure to give, after crystallisation from ethyl acetate/petrol, the title compound (E1) (1.2 g, 100%) m.p. 114°–5° C. $^1$H-NMR (CDCl$_3$) 270 MHz.

| δ | |
|---|---|
| | 8.30 (d, 1H) |
| | 8.05 (d, 1H) |
| | 7.85 (dd, 1H) |
| | 5.45–5.30 (m, 1H) |
| | 3.35–3.20 (m, 2H) |
| | 2.70–2.50 (m, 2H) |
| | 2.30 (s, 3H) |
| | 2.20–1.90 (m, 4H) |
| | 1.85–1.70 (m, 2H) |

EXAMPLE 2

(endo)-3-(8-Methyl-8-azabicyclo[3.2.1]oct-3-yl)-3,4-dihydro-4-oxo-1,2,3-benzotriazine (E2)

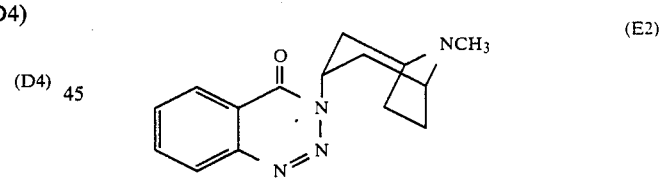

(E2)

following the procedures described in Description 1 and Example 1, isatoic anhydride was converted to the title compound E2 (overall yield 30%) m.p. 75°–6° C. $^1$H-NMR (CDCl$_3$) 270 MHz.

| δ | |
|---|---|
| | 8.33 (dm, 1H) |
| | 8.14 (dm, 1H) |
| | 7.92 (tm, 1H) |
| | 7.78 (tm, 1H) |
| | 5.36 (tt, 1H) |
| | 3.34–3.24 (m, 2H) |
| | 2.70–2.55 (m, 2H) |
| | 2.30 (s, 3H) |
| | 2.20–1.75 (m, 6H) |

EXAMPLE 3

(endo)-3-(8-Methyl-8-azabicyclo[3.2.1]oct-3-yl)-6-chloro-7-nitro-3,4-dihydro-4-oxo-benzotriazine (E3)

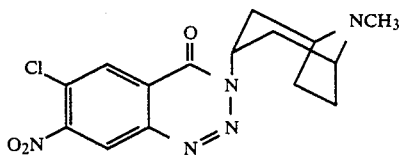

(endo)-N-(8-methyl-8-azabicyclo[3.2.1]oct-3-yl)-2-amino-5 chloro-4-nitrobenzamide (0.62 g, 0.0018 mol) was dissolved in 5N sulphuric acid (4 ml) and water (10 ml) cooled to 0° C. Sodium nitrite (0.15 g, 0.0022 mol) was added and the mixture was stirred at 0° C. for 1 hour. The mixture was basified with potassium carbonate and the product extracted into chloroform. The solution was dried over sodium sulphate and evaporated to dryness. Recrystallisation from ethylacetate/petrol yielded the title compound (0.38 g, 60%).
m.p. 193°–9° C.
$^1$H NMR (CDCl$_3$) 270 MHz.

| δ | |
|---|---|
| 8.51 | (s, 1H) |
| 8.50 | (s, 1H) |
| 5.30–5.42 | (m, 1H) |
| 3.25–3.35 | (brs, 2H) |
| 2.56–2.70 | (m, 2H) |
| 2.30 | (s, 3H) |
| 2.10–2.20 | (m, 2H) |
| 1.90–2.01 | (m, 2H) |
| 1.65–1.78 | (m, 2H) |

EXAMPLE 4

(endo)-3-(8-Methyl-8-azabicyclo[3.2.1]oct-3-yl)-7-amino-6-chloro-3,4-dihydro-4-oxo-benzotriazine (E4)

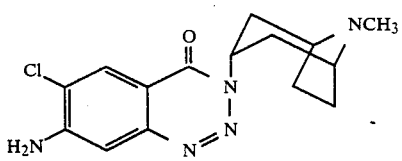

The nitro compound E3 (0.5 g, 0.014 mol) was hydrogenated at atmospheric pressure and at 20° C. in ethanol (100 ml) over raney nickel (acid washed). After 1 hour the catalyst was filtered off and the filtrate evaporated to dryness. The residue was extracted into methylene chloride, dried over sodium sulphate and evaporated to dryness. The residue was purified by column chromatography on alumina, eluting with chloroform. Recrystallisation from ethyl acetate/petrol gave the title compound (0.1 g, 22%)
m.p. 200°–1° C.
$^1$H NMR (CDCl$_3$) 270 MHz.

| δ | |
|---|---|
| 8.32 | (s, 1H) |
| 7.40 | (s, 1H) |
| 5.36–5.48 | (m, 1H) |
| 4.95 | (brs, 2H) |
| 3.33–3.43 | (brs, 2H) |
| 2.63–2.79 | (m, 2H) |
| 2.31 | (s, 3H) |
| 2.17–2.25 | (m, 2H) |
| 2.04–2.12 | (m, 2H) |
| 1.85–1.95 | (m, 2H) |

EXAMPLE 5

(endo)-3-(9-Methyl-9-azabicyclo[3.3.1]non-3-yl)-6-chloro-7-nitro-3,4-dihydro-4-oxobenzotriazine (E5)

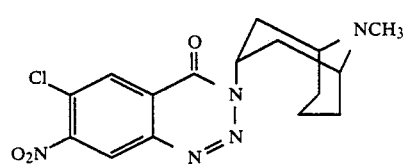

Following the general procedure outlined in example 1, (endo)-N-(9-methyl-9-azabicyclo[3.3.1]non-3-yl)-2-amino-5-chloro-4-nitrobenzamide was converted to the benzotriazole E5 (0.75 g, 55%).

EXAMPLE 6

(endo)-3-(9 Methyl)-9-azabicyclo[3.3.1]non-3-yl)-7-amino-6-chloro-3,4-dihydro-4-oxobenzotriazine (E6)

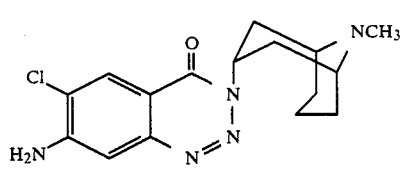

(endo)-3-(9-Methyl-9-azabicyclo[3.3.1]nonan-3-yl)-6-chloro-7-nitro-3,4-dihydro-4-oxobenzotriazine (0.75 g) was hydrogenated as in example 4 to yield the title compound (0.36 g, 53%).
m.p. 224°–6° C.
$^1$H NMR (DMSO-d$^6$).

| δ | |
|---|---|
| 8.11 | (s, 1H) |
| 7.37 | (s, 1H) |
| 5.95 | (brs, 2H) |
| 5.54–5.70 | (m, 1H) |
| 3.20–3.30 | (brd, 2H) |
| 2.60 | (s, 3H) |
| 2.31–2.47 | (m, 2H) |
| 1.99–2.28 | (m, 5H) |
| 1.52–1.66 | (m, 1H) |
| 1.11–1.22 | (m, 2H) |

Following the procedures outlined in, where appropriate, Examples 1, 3 and 4, the following compounds were prepared.

EXAMPLE 7

(5β)-3-(2-Methyl-2-azabicyclo[2.2.2]oct-5-yl)-6-chloro-3,4-dihydro-4-oxobenzotriazine (E7)

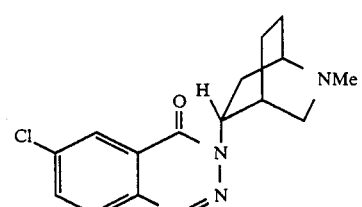

m.p. 94–98° C.

| $^1$H-Nmr (CDCl$_3$) δ: |
|---|
| 8.30 (d, 1H) |
| 8.10 (d, 1H) |
| 7.88 (dd, 1H) |
| 5.26–5.17 (m, 1H) |
| 2.99–2.82 (m, 3H) |
| 2.79–2.72 (m, 1H) |
| 2.46 (s, 3H) |
| 2.19–1.75 (m, 5H) |
| 1.72–1.59 (m, (1H) |

EXAMPLE 8

(5β)-3-(2-Methyl-2-azabicyclo[2.2.2]oct-5-yl)-7-amino-6-chloro-3,4-dihydro-4-oxobenzotriazine (E8)

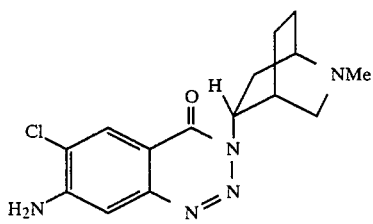
(E8)

m.p. 290–5° C.

| $^1$H-Nmr (d$^6$-DMSO) δ: |
|---|
| 8.03 (s, 1H) |
| 7.39 (s, 1H) |
| 6.38 (brs, 2H) |
| 5.30–5.18 (m, 1H) |
| 3.55 (brs, 1H) |
| 3.00–2.75 (m, 5H including 2.89, s, 3H) |
| 2.55–2.28 (m, 3H) |
| 2.05–1.80 (m, 4H) |

EXAMPLE 9

3-(1-Azabicyclo[2.2.2]oct-3-yl)-7-amino-6-chloro-3,4-dihydro-4-oxobenzotriazine (E9)

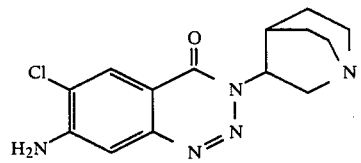
(E9)

m.p. 243–6° C.

| $^1$H-Nmr (d$^6$-DMSO) δ: |
|---|
| 7.99 (s, 1H) |
| 7.31 (s, 1H) |
| 6.59 (brs, 2H) |
| 5.12–5.02 (m, 1H) |
| 3.47 (dd, 1H) |
| 3.26 (t, 1H) |
| 3.12–2.95 (m, 1H) |
| 2.89–2.70 (m, 3H) |
| 2.12–2.03 (m, 1H) |
| 1.85–1.60 (m, 3H) |
| 1.45–1.30 (m, 1H) |

EXAMPLE 10

(endo)-3-(8-Methyl-8-azabicyclo[3.2.1]oct-2-yl)-7-amino-6-bromo-3,4-dihydro-4-oxobenzotriazine (E10)

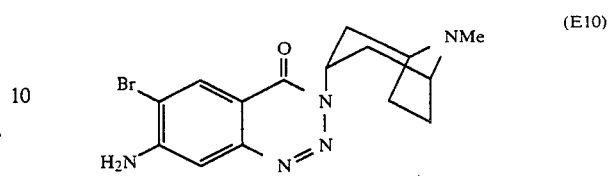
(E10)

m.s. M$^+$ 363, 365

| $^1$H-Nmr (CDCl$_3$) δ: |
|---|
| 8.40 (s, 1H) |
| 7.26 (s, 1H) |
| 5.32 (dt, 1H) |
| 4.90 (brs, 2H) |
| 3.28 (brs, 2H) |
| 2.70–2.50 (m, 2H) |
| 2.30 (s, 3H) |
| 2.15–2.02 (m, 2H) |
| 1.96 (dd, 2H) |
| 1.85–1.70 (m, 2H) |

EXAMPLE 11

(endo)-3-(8-Methyl-8-azabicyclo[3.2.1]oct-3-yl)-6chlor-7-nitro-3,4-dihydro-4-oxoquinazoline (E11)

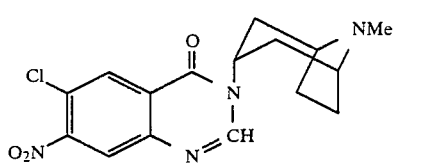
(E11)

A mixture of intermediate D3 (0.44 g), conc. H2SO4 (2 drops) and triethylorthoformate (10m) was heated under reflux for 30h. The reaction mixture was evaporated to dryness and the residue partitioned between CHCl3 (50ml) and NaHC03 solution (20 ml). The separated organic layer was dried (K2CO3), evaporated to dryness and the residue purified by column chromatography on alumina, eluting with CHCl3, to give the title compound (0.22 g).

m.s. M+348.350.

| $^1$H-Nmr (CDCl$_3$) δ: |
|---|
| 8.43 (s, 1H) |
| 8.11 (s, 1H) |
| 8.07 (s, 1H) |
| 4.89 (tt, 1H) |
| 3.40–3.30 (m, 2H) |
| 2.63–2.48 (m, 2H) |
| 2.30–2.15 (m, 5H including 2.24, s, 3H) |
| 1.82–1.60 (4H) |

EXAMPLE 12

(endo)-3-(8-Methyl-8-azabicyclo[3.2.1]oct-3-yl)-7-amino-6-chloro-3,4-dihydro-4-oxoquinazoline (E12)

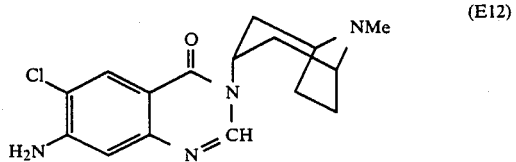

Following the procedures outlined in Example 4, the nitro compound (E11) (0.21 g) was converted to the title compound (0.15 g). m.s. 318,320.

| $^1$H-Nmr (CDCl$_3$)δ: |
|---|
| 8.16 (s, 1H) |
| 7.92 (s, 1H) |
| 6.89 (s, 1H) |
| 4.77 (tt, 1H) |
| 4.60 (brs, 2H) |
| 3.35–3.25 (m, 2H) |
| 2.60–2.42 (m, 2H) |
| 2.28–2.12 (m, 5H including 2.22, s, 3H) |
| 1.85–1.70 (m, 4H) |

PHARMACOLOGY

Antagonism of the von Bezold-Jarisch reflex

The compounds were evaluated for antagonism of the von Bezold-Jarisch reflex evoked by 5-HT in the anaesthetised rat according to the following method:

Male rats, 250–350 g, were anaesthetised with urethane (1.25 g/kg intraperitoneally) and blood pressure and heart rate recorded as described by Fozard J.R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5HT-evoked response to 50% of the control response (ED$_{50}$) was then determined.

The results were as follows:

| Compound | ED$_{50}$ μg/kg i.v. |
|---|---|
| E1 | 12 |
| E3 | 13 |
| E4 | 0.17 |
| E8 | 6 |

I claim:

1. A compound of formula (I), or a pharmaceutically acceptable salt thereof:

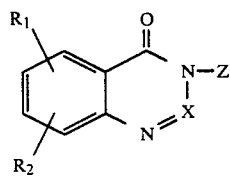

wherein
X is N;
R$_1$ and R$_2$ are the same or different and are hydrogen, halogen, CF$_3$, C$_{1-6}$ alkyl, C$_{1-7}$ acyl, C$_{1-7}$ acylamino, or amino, aminocarbonyl or aminosulphonyl, optionally substituted by one or two C$_{1-6}$ alkyl or C$_{3-8}$ cycloalkyl groups, or by C$_{4-5}$ polymethylene or by phenyl, C$_{1-6}$ alkylsulphonyl, C$_{1-6}$ alkylsuphinyl, C$_{1-6}$ alkoxy, C$_{1-6}$ alkylthio, hydroxy or nitro; or R$_1$ and R$_2$ taken together are methylenedioxy or ethylenedioxy;

Z is a group of formula (a), (b) or (c)

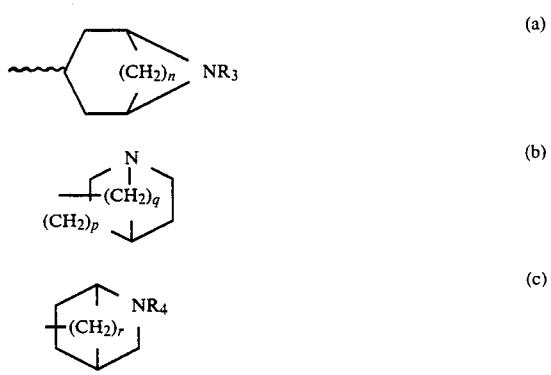

wherein
n is 2 or 3; p is 1 or 2; q is 1 to 3; r is 1 to 3; and R$_3$ or R$_4$ is C$_{1-4}$ alkyl.

2. A compound according to claim 1 of formula (II):

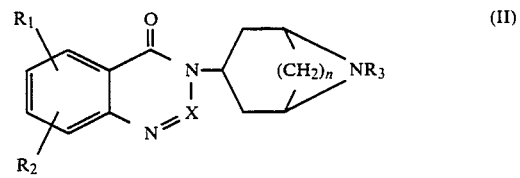

wherein R$_1$, R$_2$, R$_3$, X and n are as defined in claim 1.

3. A compound according to claim 2 wherein n is 2.

4. A compound according to claim 2 wherein R$_3$ or R$_4$ is methyl.

5. A compound according to claim 1 of formula (III):

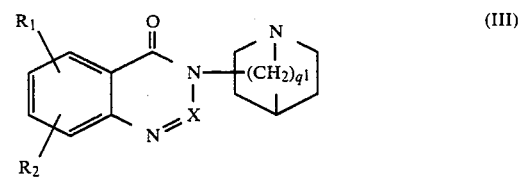

wherein q$^1$ is 1 or 2 and R$_1$, R$_2$ and X are as defined in claim 1.

6. A compound according to claim 5 wherein q is 2.

7. A compound according to claim 1 wherein R$_1$ is hydrogen, 7-chloro or 7-bromo and R$_2$ is hydrogen; or R$_1$ is 7-amino and R$_2$ is 6-chloro or 6-bromo.

8. A compound selected from the group consisting of
(endo)-3-(8-methyl-8-azabicyclo[3.2.1]oct-3-yl)-6-chloro-3,4-dihydro-4-oxo-1,2,3-benzotriazine,
(endo)-3-(8-methyl-8-azabicyclo[3.2.1]oct-3-yl)-3,4-dihydro-4-oxo-1,2,3-benzotriazine,
(endo)-3-(8-methyl-8-azabicyclo[3.2.1]oct-3-yl)-6-chloro-7-nitro-3,4-dihydro-4-oxo-1,2,3-benzotriazine, (endo)-3-(8-methyl-8-azabicyclo[3.2.1]oct-3-yl]-7-amino-6-chloro-3,4-dihydro-4-oxo-1,2,3-benzotriazine, (endo)-3-(9-methyl-9-azabicyclo[3.3.1]non-3-yl)-6-chloro-7-nitro-3,4-dihydro-4-oxo-1,2,3-benzotriazine, (endo)-3-(9-methyl-9-azabicyclo[3.3.1]non-3-yl)-7-amino-6-chloro-3,4-dihydro-4-oxo-1,2,3-benzotriazine, (5β)-3-(2-methyl-2-azabicyclo[2.2.2]oct-5-yl)-6-chloro-3,4-dihydro-4-oxo-1,2,3-benzotriazine, (5β)-3-(2-methyl-2-azabicyclo[2.2.2]oct-5-yl)-7-amino-6-chloro-3,4-dihydro-4-oxo-1,2,3-benzotriazine, 3-(1-azabicyclo[2.2.2]oct-3-yl)-7-amino-6-chloro-3,4-dihydro-4-oxo-1,2,3-benzotriazine, (endo)-3-(8-methyl-8-azabicyclo[3.2.1]oct-2-yl)-7-amino-6-bromo-3,4-dihydro-4-oxo-1,2,3-benzotriazine, or a pharmaceutically acceptable salt of any of the foregoing.

9. A pharmaceutical composition comprising a 5-HT$_3$ antagonist effective amount of a compound according to claim 1 and a pharmaceutically acceptable carrier.

10. A method of treatment of emesis, migraine, cluster headache, trigeminal neuralgia, visceral pain or anxiety in mammals, which comprises the administration of an effective amount of a compound according to claim 1.

* * * * *